United States Patent [19]
Coppock et al.

[11] Patent Number: 5,503,158
[45] Date of Patent: Apr. 2, 1996

[54] AMBULATORY ELECTROCARDIOGRAM MONITOR

[75] Inventors: Richard A. Coppock; Irving Rosenbluth, both of San Jose, Calif.

[73] Assignee: CardioCare, Inc., Los Altos Hills, Calif.

[21] Appl. No.: 294,132

[22] Filed: Aug. 22, 1994

[51] Int. Cl.⁶ .................................................. A61B 5/04
[52] U.S. Cl. ................... 128/696; 128/710; 128/695 R; 128/639
[58] Field of Search .................... 128/695, 696, 128/697, 698, 700, 701, 709, 710, 903, 639, 902

[56] References Cited

U.S. PATENT DOCUMENTS

| | | | |
|---|---|---|---|
| 3,724,455 | 4/1973 | Unger | 128/903 X |
| 4,494,551 | 1/1985 | Little, III et al. | 128/696 |
| 4,622,979 | 11/1986 | Katchis et al. | 128/702 |
| 4,905,706 | 3/1990 | Duff et al. | 128/700 X |
| 4,981,141 | 1/1991 | Segalowitz | 128/696 |
| 5,012,411 | 4/1991 | Policastro et al. | 364/413.06 |
| 5,113,869 | 5/1992 | Nappholz et al. | 128/903 X |
| 5,224,479 | 7/1993 | Sekine | 128/639 X |
| 5,231,990 | 7/1983 | Gauglitz | 127/697 |
| 5,280,791 | 1/1994 | Lavie | 128/696 |

FOREIGN PATENT DOCUMENTS

405042117  2/1993  Japan ................. 128/709

*Primary Examiner*—Angela D. Sykes
*Assistant Examiner*—Steve Huang
*Attorney, Agent, or Firm*—Flehr, Hohbach, Test, Albritton & Herbert

[57] ABSTRACT

An electrocardiogram monitor comprises a plurality of sensors placed on the patient's skin to generate a sensor signal indicative of the patient's heartbeat. An amplifier is connected to the plurality of sensors, in close proximity thereto, to amplify the sensor signal and generate an amplified signal. A processor remote from the sensors, having a receiver is connected to the amplifier to receive the amplified signal and to process the amplified signal to obtain the patient's electrocardiogram.

35 Claims, 6 Drawing Sheets

AMBULATORY ELECTROCARDIOGRAM MONITOR

FIELD OF THE INVENTION

The present invention relates to an apparatus and method for monitoring a patient's electrocardiogram.

BACKGROUND OF THE INVENTION

Electrocardiogram (ECG) signal monitoring is important for understanding a patient's heart condition. Since a patient's skin exhibits voltage differences due to the muscle contractions of the heart, ECG signal acquisition involves strategically placing several electrode sensors on a patient and then evaluating the electrical signals from the sensors. A typical sensor includes a metal contact with conductive gel and attaches to the patient's skin with an adhesive bandage. The sensor generates sensor signals indicative of the skin voltages that represent the heart contractions. These sensor signals are fed to a recorder which may store them or print them out on a roll of paper.

ECG signal acquisition hardware designers are faced with problems of uncertain skin/electrode resistance and undesired noise induced by neighboring electromagnetic fields. One problem arises because skin signal voltage is on the order of 1 mV and must be amplified approximately 1000× before processing. This small signal is susceptible to stray interference effects. The conventional approach to handling these problems is to invoke a rigorous skin preparation - including shaving skin, abrasion, and cleaning with isopropyl alcohol - and to limit the signal bandwidth to a span of 0.05 to 40 Hz to avoid 60 and 120 Hz interference.

Ambulatory out-patient monitors have these problems and more. Patients do not always follow a physician's instructions on scrubbing the skin and properly applying the sensors. Often, this causes noise that results in poor signal quality and lost data. Also, monitoring a patient's ECG while outside the hospital or physician's office may involve recording the ECG over long periods of time, which requires large data memory. Often, this large amount of data requires that the patient personally visit the hospital or office for the ECG data to be analyzed. Moreover, few devices allow the patient to identify when a cardiac episode occurred, permitting the doctor to analyze that specific ECG segment without reviewing the entire data record.

A monitor that can improve the signal-to-noise ratio of the heartbeat signal and that can efficiently record cardiac episodes would be helpful in diagnosing and correcting a patient's cardiac problem.

SUMMARY OF THE INVENTION

An electrocardiogram monitor comprises a plurality of sensors placed on the patient's skin to generate a sensor signal indicative of the patient's heartbeat. An amplifier is connected to the plurality of sensors, in close proximity thereto, to amplify the sensor signal and generate an amplified signal. A processor remote from the sensors having a receiver is connected to the amplifier to receive the amplified signal and to process the amplified signal to obtain the patient's electrocardiogram.

An advantage of the invention is that it is easy for an out-patient to use at home or away from the hospital by reducing the skin and sensor preparation required by prior systems.

Another advantage of the invention is that it identifies and stores episodes of irregular electrocardiogram signals that can be replayed to a doctor for evaluation, An advantage of one aspect of the invention is that it permits a conveniently small sized monitor that provides a patient freedom of movement by transmitting an amplified signal from a patient via RF waves to a base unit that records the ECG signal.

BRIEF DESCRIPTION OF THE DRAWINGS

The objects and advantages of the invention will become apparent upon reading the following detailed description and upon reference to the drawings, in which.

DETAILED DESCRIPTION OF PREFERRED EMBODIMENTS

Preferred embodiments are described with reference to specific configurations, Those skilled in the art will appreciate that various changes and modifications can be made to the preferred embodiments while remaining within the scope of the present invention, A first embodiment of an electrocardiogram (ECG) monitor is described with reference to FIGS. 1, 2 and 3A–B. There are two main parts, the sensor assembly 100 and the processor 200, which communicate over a sensor cable 118. The processor provides power to the sensor assembly and the sensor assembly provides an ECG signal to the processor.

Figure 1:
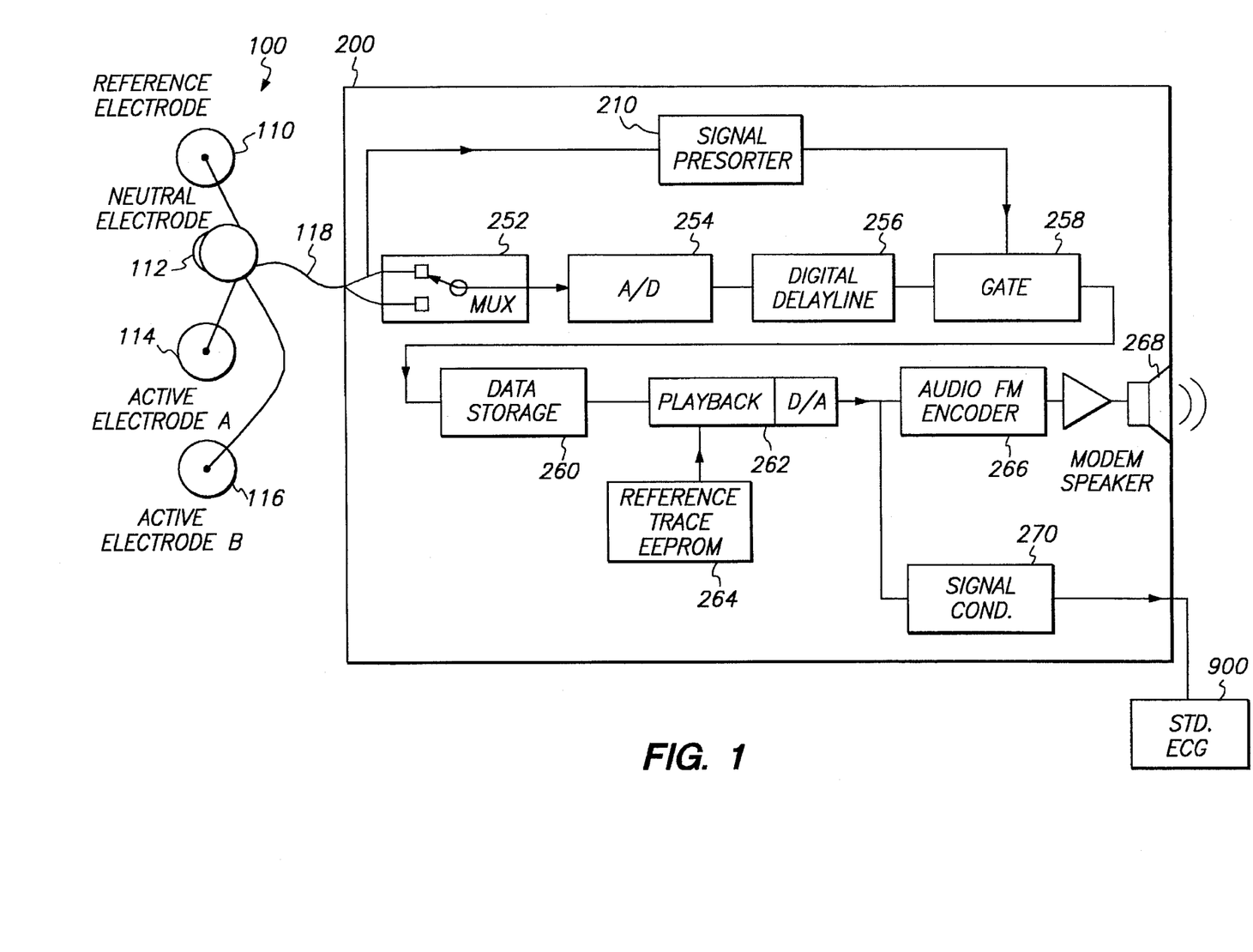
FIG. 1 depicts a first embodiment of an electrocardiogram monitor employing the present invention.
Figure 2:
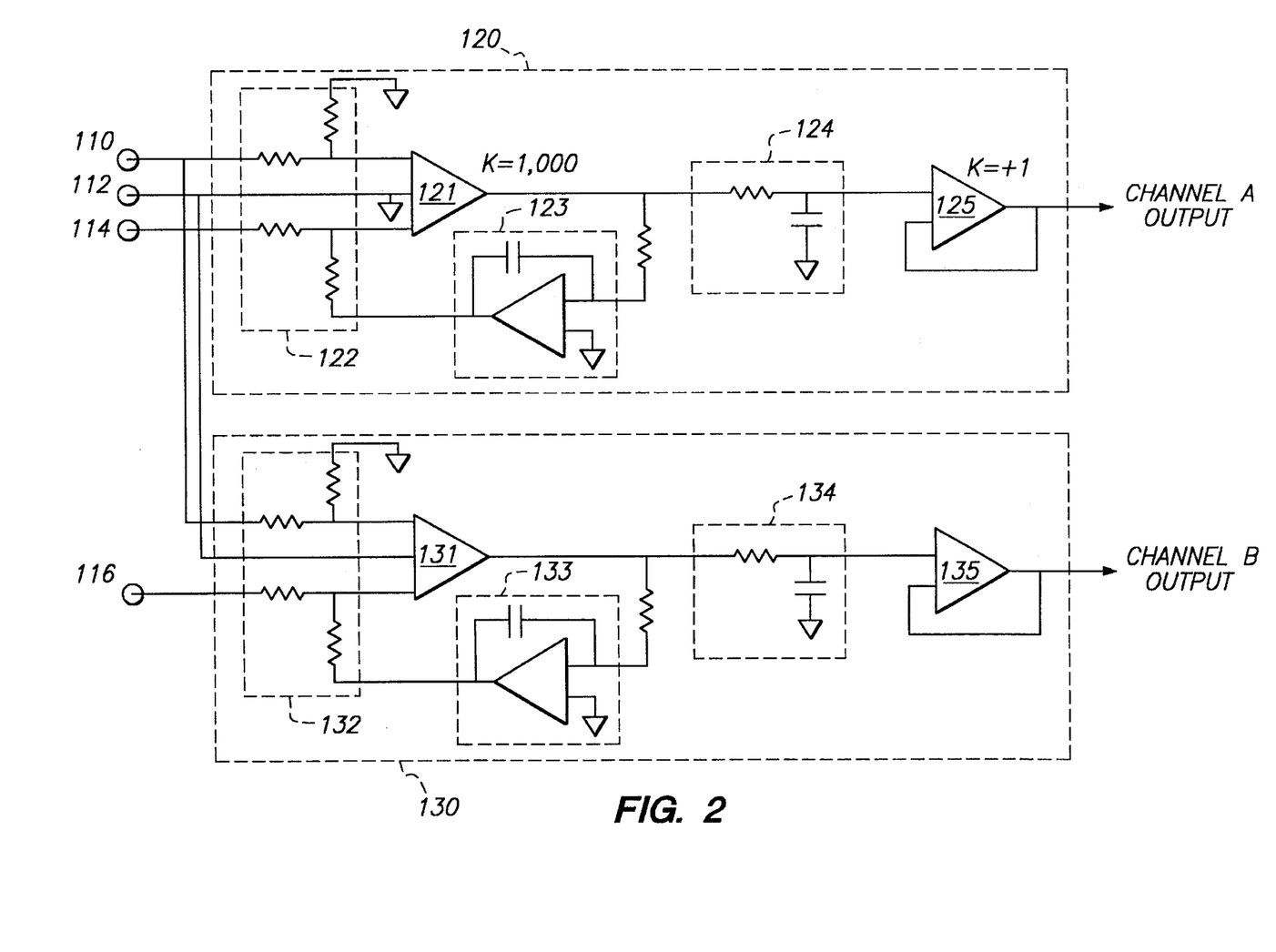
FIG. 2 shows a schematic of the sensor assembly of FIG. 1.

The sensor assembly 100 includes a reference electrode 110, a neutral electrode 112 and an active electrode 114. The electrodes are placed on a patient's skin at predetermined positions. These positions are known in the art and often vary according to the specific type of cardiac problem that a doctor is attempting to diagnose or the location of a suspected problem. Regardless of the position, however, the contact between the skin and the sensor often suffers due to lack of adequate conductivity between the skin and the sensor resulting in a low signal to noise ratio.

To overcome the problem of a low signal to noise ratio, an amplifier is incorporated in the sensor array to amplify the sensor signal. This is particularly helpful with out-patients since the patient may fail to adequately prepare the electrode sites. As shown in FIG. 2, the sensors 110, 112 and 114 are connected to an amplifier 120 that receives the signals, combines the signals, and amplifies the combined signal to a level that can be adequately handled by the processor 200. Therefore, even when a patient inadvertently fails to follow exacting procedures for obtaining optimum signal contact, the ECG signal is still acceptable and the processor 200 connected to the amplifier output is able to function properly.

FIG. 2 shows two signal paths: a channel A path and a channel B path. These paths incorporate identical circuitry and share some of the sensor outputs including the reference electrode 110 and the neutral electrode 112. The circuitry is shown using standard elements for resistors, capacitors and operational amplifiers.

Concentrating on channel A, the sensors 110, 112 and 114 are connected to the amplifier 120 and transmit sensor signals representing the skin voltage to the amplifier 120 via wires in trunk 118. An instrumentation amplifier 121 has a balanced input network 122 which preserves excellent common mode rejection (CMR), typically exceeding 100 dB. Moreover, the neutral sensor also serves to stabilize the DC CMR of the amplifier. Examples of an instrumentation amplifier that can be used in the present invention are a Burr Brown INA118 or an Analog Devices AD620.

These advantages are more fully appreciated when the sensor assembly is optimally configured by placing the amplifier 120 on the neutral electrode 112 to keep the electrode wire length at a minimum and to take advantage of the Faraday-shielding effect of the patient's body to minimize interfering signals. The umbilical cable arrangement, where power to the amplifier 120 travels in the same cable trunk as the amplified signal, also reduces the effect of low-level interference which may be generated in the processor 200.

Two features ensure fast recovery of the circuit toward stabilized operation. First, the neutral electrode 112 establishes the midpoint of the DC common-mode operating range. Second, the high-pass filter requirement is accomplished with a feedback integrator 123, rather than a conventional RC network. The high closed-loop DC feedback gain of amplifier 120 incorporating amplifiers 121 and 123 provides slew-rate transient recovery, rather than a much slower exponential recovery expected with an RC network.

The amplifier 120 output is connected to a low pass filter 124 to reduce any interference and high frequency noise. For example, an upper cutoff band of equal to or greater than 150 Hz works well in this embodiment. The low pass filter 124 is connected to a buffer amplifier 125. The buffer amplifier serves to transmit the amplified signal with reverse isolation for optimal signal transmission.

Also shown in FIG. 2 is the channel B path, shown by amplifier 130. This path begins with the second active sensor 116 and shares the reference sensor 110 output and neutral sensor 112 output. Although the channel B path is optional, it can help in diagnosing the patient because it can provide another point of reference for an ECG. The sensors 110, 112 and 116 transmit sensor signals to amplifier 130 via wires. The amplifier 130 is similar to amplifier 120 and has a balanced input network similar to amplifier 120.

This sensor assembly design overcomes many of the problems identified in the background by pre-amplifying the sensor signals. This novel concept alleviates the need to carefully prepare the skin. This design permits a sensor to simply be placed over the skin in order to work properly, which is a valuable asset to ambulatory monitors.

The processor 200 includes a receiver multiplexer 252 that selects to receive either the amplified signal from the channel A buffer amplifier 125 or the channel B buffer amplifier 135. The selected amplified signal is delivered to an analog to digital (A/D) converter 254, while the channel A signal, typically from the V5 lead, is delivered to the presorter 210 input.

Figure 3A:
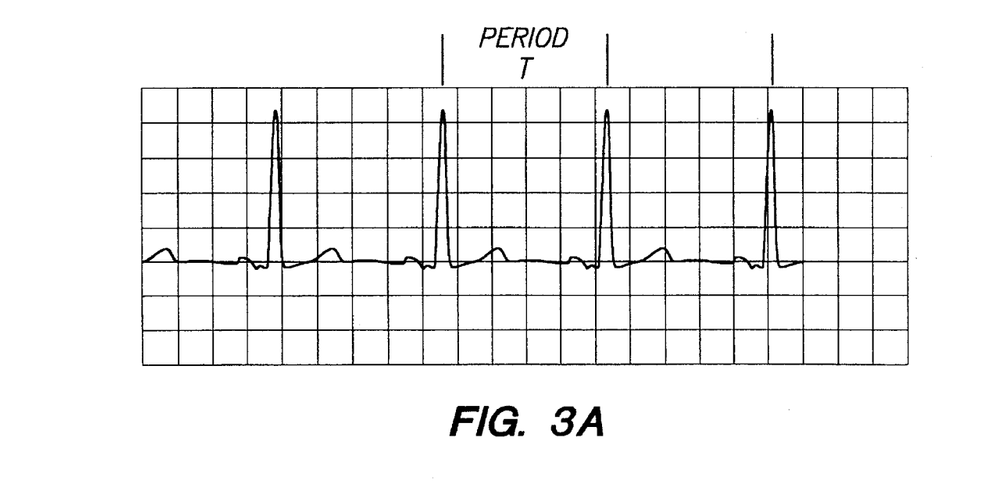
FIG. 3A is a graph of a typical electrocardiogram.

A sample ECG signal is shown in FIG. 3A. These peaks indicated in the signal are the most suitable (i.e. precise) temporal reference points for the ECG waveform. The signal presorter 210 is responsible for tracking the amplified signal and determining if there is an abnormality. In this context, an abnormality includes arrhythmia, temporal changes or amplitude displacements of key features, e.g., S-T segment depression.

Figure 3B:
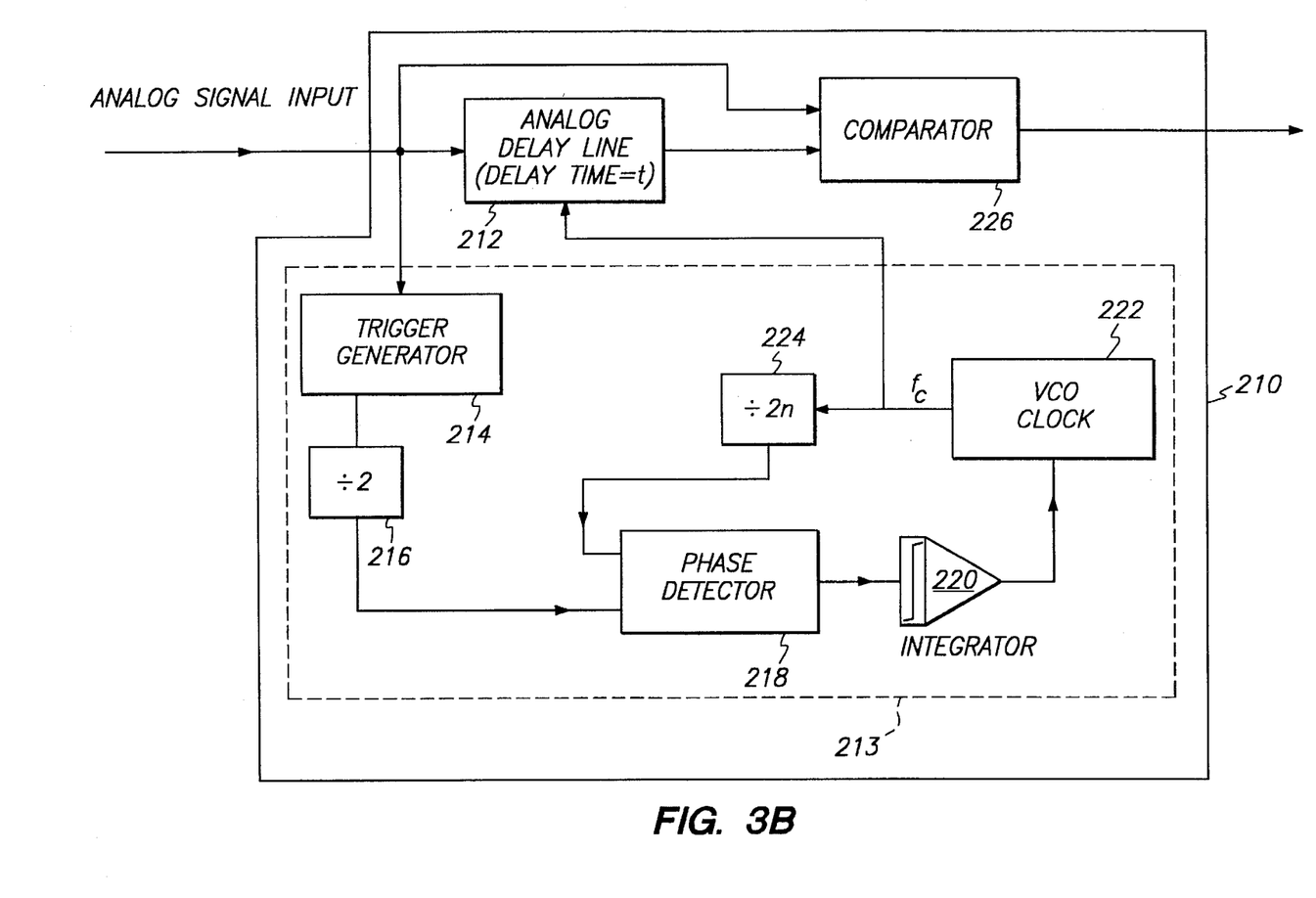
FIG. 3B shows a schematic of a signal presorter of FIG. 1.

The signal presorter 210 operates by identifying a signal that differs in time or amplitude from its predecessor so that the abnormal signal can be recorded. An analog delay line 212 is used to delay the amplified signal by a time interval (t), varied by the tracker to match the R-R interval (T). This is accomplished by the pulse period tracker 213 that essentially operates as a frequency/phase phase-locked loop. A trigger generator 214 produces a trigger which accurately corresponds to the R-segment peak. This triggers a divide-by-two flip-flop 216 generating one square wave input to phase detector 218. The frequency is 1/(2T).

The other square wave input to square wave detector 218 is provided by VCO 222 and a divide-by-two-n counter 224. This frequency is 1/(2t). Since n is the number of elements in the analog delay line 212, t≡T when the loop acquires lock. The phase-locked loop is completed by error signal integrator 220. The implementation incorporates a Type II phase detector which does not lock on harmonics or subharmonics, a necessity since the anticipated range of operation is far beyond an octave (30–200 beats per minute).

The number n is related to the analog delay line 212, which is typically 1024 as provided, for example, by an EGG Reticon RD5108A device.

The analog delay line 212 and pulse period tracker 213 provide a running replica of the input analog signal delayed by exactly one R-R interval or heartbeat period. This represents a prior ECG. The real-time signal stream and delayed signal stream are continuously compared by analog comparator 226. When the comparator 226 notices a difference between the analog signal input and the analog delay line output - an abnormality - the comparator activates the gate 258.

Figure 3C:
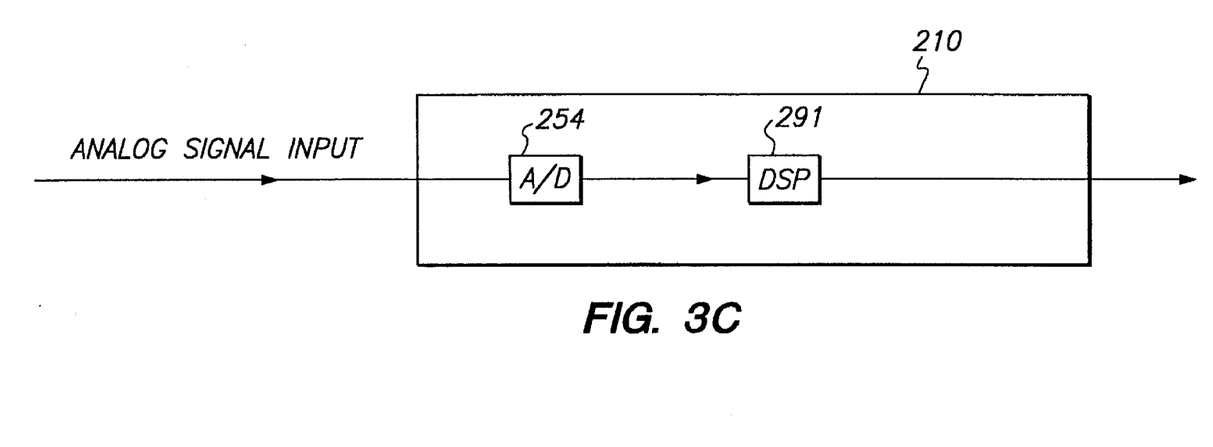
FIG. 3C shows a schematic of an alternative signal presorter of FIG. 1.

Alternatively, as shown in FIG. 3C, the signal presorter 210 can be performed using a digital signal processor (DSP) 291. This alternative takes the A/D converter 254 output and manipulates the data to perform processing similar to that described with respect to the analog circuit of FIG. 3B. The DSP 291 uses a portion of its memory to store prior ECG samples and then compares the stored samples against the present-time samples looking for an abnormality. An example of a DSP that can accomplish this task is the Texas Instruments TMS320.

The gate 258 has been receiving a digital data signal that was converted in the A/D convertor 254 and then temporarily stored in a digital delay line 256. The digital delay line is essentially a first in first out (FIFO) memory. If the signal presorter determines that an abnormality has occurred, the gate is activated and the delayed data in the digital delay line is stored in data storage 260.

This embodiment advantageously stores data from before the abnormality and for a period of time after the abnormality. For example, the digital delay line 256 can be configured to store 5–10 seconds of data in its FIFO memory. Then, when an abnormality occurs, that 5–10 seconds of data is stored in data storage 260 along with a period of time thereafter, for example, 5–10 seconds.

An advantage of this type of recording is that when the heartbeat is regular - no abnormality - the data is not stored, and that when an abnormality does occur, data from before, during and after the abnormality is recorded. This directly reduces the amount of data that needs to be stored, and it efficiently stores the most relevant data for later evaluation by a doctor.

Another feature of the first embodiment is the playback of the stored data. When required, the data storage 260 outputs the stored data and it is played back through playback digital to analog (D/A) converter 262. A personal reference trace read only memory 264 (EEPROM) may also be incorporated to play back a personal reference trace preamble to give a doctor an example of the patient's normal ECG signal. This preamble helps the doctor to compare the present-time ECG with the individual patient's normal ECG.

The data is converted back to its original form through payback D/A 262 and is sent to an audio encoder 266 to create an audio signal on speaker 268 for transtelephonic communication, and sent through a signal conditioner 270 to an external standard ECG display 900. The data can also be sent directly over the telephone line by a modem as an electrical signal. The playback feature permits a doctor to efficiently evaluate the data stored by the processor 200. Moveover, the processor 200 can communicate with any commercial ECG display so that even when the patient must go to an unfamiliar hospital, a doctor with a standard ECG monitor can read the stored data.

A useful device for performing the A/D conversion, data storage control, and D/A conversion is an integrated circuit such as the Oki MSM6388 or MSM6588 or the Samsung KS5915. While these circuits have traditionally been used in telephone answering equipment, they have the capability to efficiently perform the functions taught by the present invention.

Figure 4:
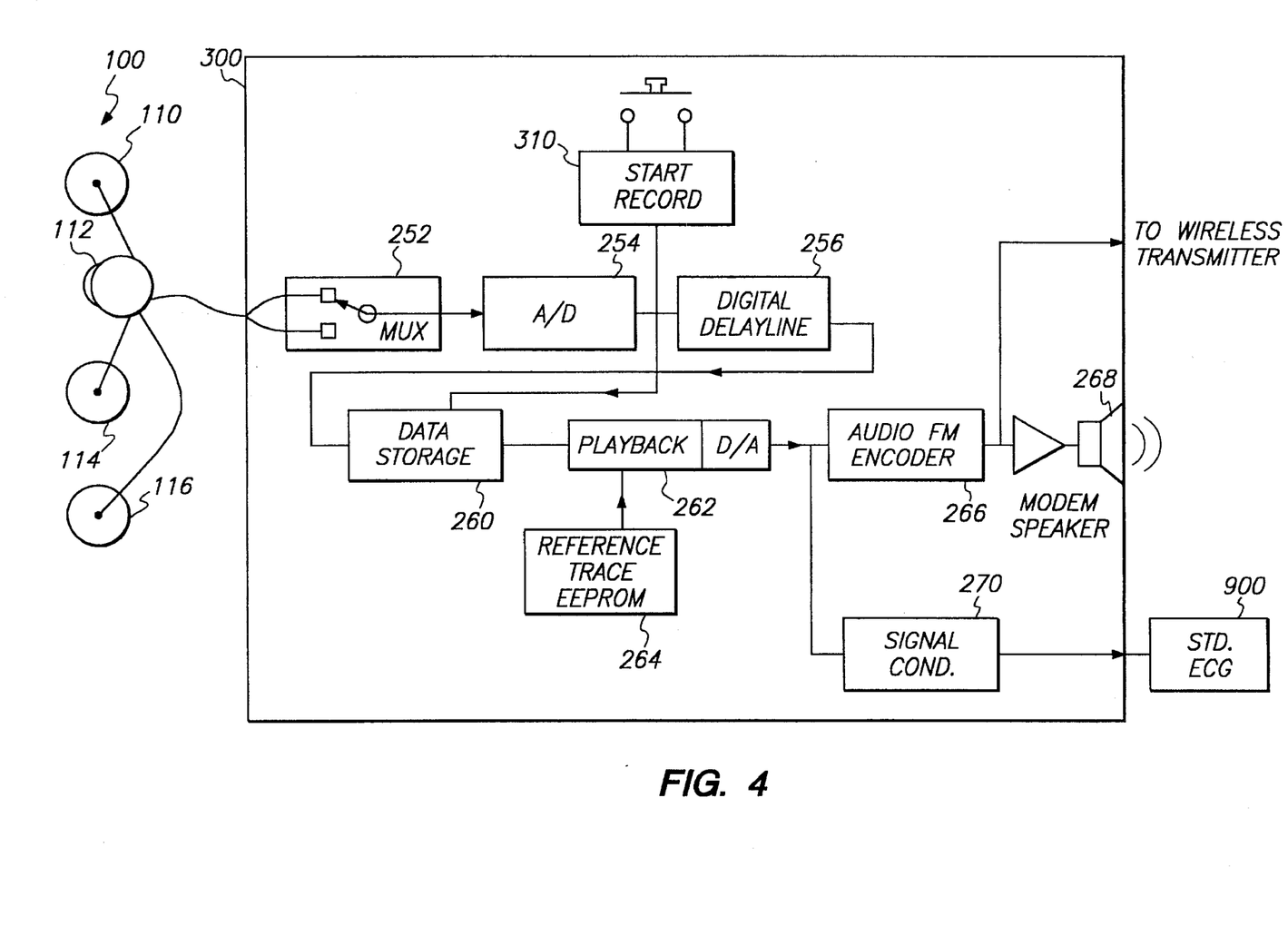
FIG. 4 depicts a second embodiment of an electrocardiogram monitor employing the present invention.

A second embodiment is shown in FIG. 4. This embodiment is similar to that shown in FIG. 1, except the signal presorter 210 and gate 258 are replaced with a button 310. The button 310 is for a patient to signal the processor 300 when the patient feels a cardiac episode. Thus, if the patient feels faint, weak or chest pains, the patient presses the button 310 and the processor 300 stores delayed data and the digital data signal. For example, the previous 90 seconds and next 60 seconds are recorded in the data storage 260. The doctor can evaluate the ECG from the time of the incident and evaluate the patient's heart condition.

This second embodiment of the monitor with the button 310 can also be combined with the first embodiment signal presorter 210 by adding the button of the first embodiment and activating the gate 258 when the patient presses the button 310.

Figure 5A:
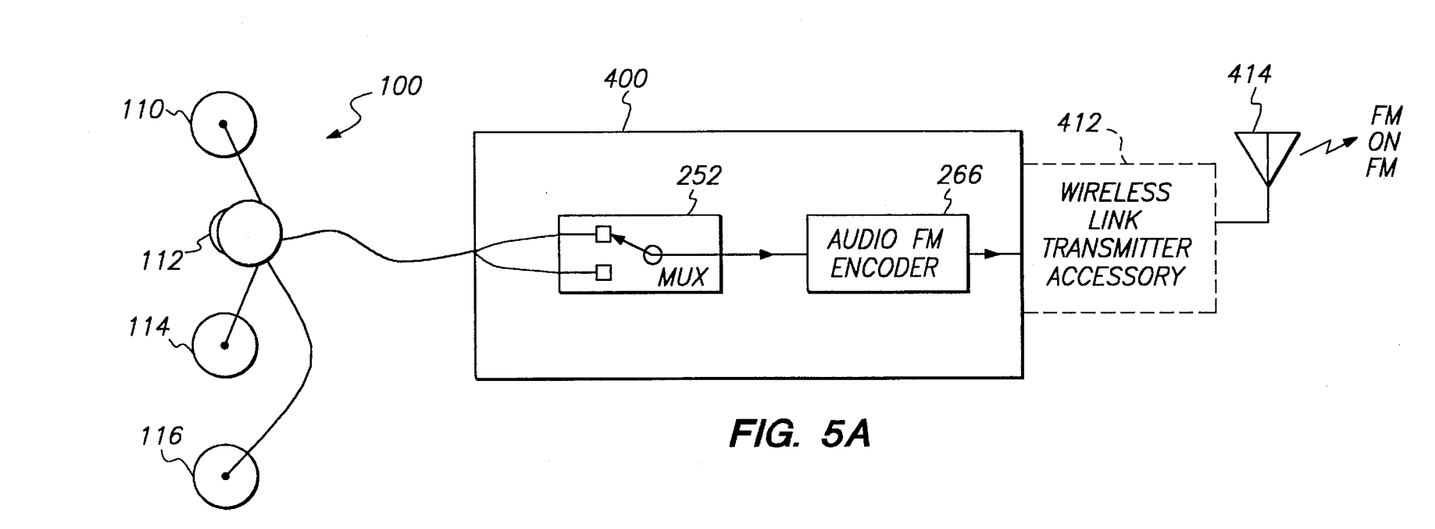
FIGS. 5A–B depict a third embodiment of an electrocardiogram monitor employing the present invention.
Figure 5B:
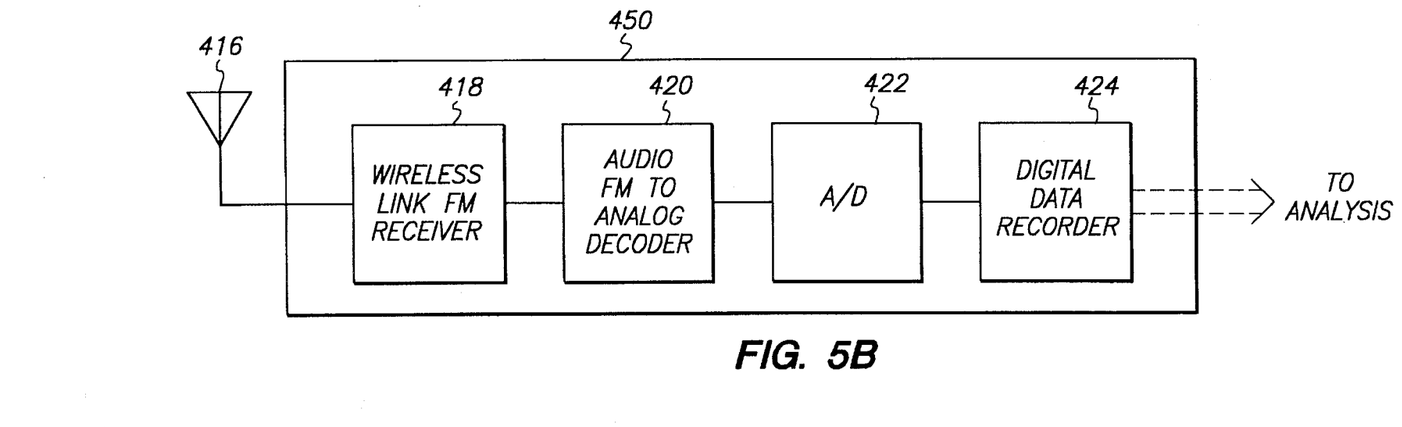

A third embodiment is shown in FIGS. 5A and 5B. This embodiment is helpful for a person who desires to have the freedom to move without the restraint of a processor. This is beneficial, for example, when a person is sleeping. A sensor array 100 is similar to that described above, and is connected to a transmitter unit 400. The transmitter unit continuously receives the amplified signal from the sensor array 100, selects a path option with multiplexer 252, and modulates the baseband amplified signal onto an audio FM sub-carrier (approximately 1.5–3 KHz) in the audio FM encoder 410, which then modulates a short-range FM RF carrier in transmitter 412. This FM-FM encoded signal is transmitted via an antenna 414 to a base unit 450.

The base unit 450 receives the encoded signal via antenna 416 and demodulates it to audio FM by receiver 418. The signal is then decoded by the audio FM decoder 420, which can be performed by a National Semiconductor LM2917. Decoder 420 then delivers the signal to an A/D converter 422 which, for example, supplies a 10-bit conversion. Thereafter, the digital samples are stored by digital data recorder 424 for later analysis by a physician or other health-care provider. The storage can be accomplished on a small hard-disk through a PCMCIA, or similar, interface. This high-capacity recorder has the capability to provide full-disclosure recording.

Alternately, after the signal is converted by the A/D 254 converter as in FIG. 1, processing is conducted as in the previously disclosed first embodiment. This reduces the amount of data required for storage and later review by a physician.

The advantages to this setup include that the patient can be mobile and can sleep comfortably without having an ECG storage unit restraining their movement.

In all the embodiments, a power-save feature can be incorporated. Since the sample rate of the A/D converter 254 is approximately 2K to 5K samples per second, there exists an idle time between the sample-taking during which the circuit does not need full power. This is because the time required to take a sample is only approximately 4 µs, while the idle time between samples is 500 µs to 200 µs. A power-save feature reduces the power to the circuit during this idle time. For example, the A/D converter 254 could be completely powered off, while the digital delay line 256, gate 258 and data storage could by placed into a data-hold low power mode where the data is safe, but the interface circuitry is powered off. Many integrated circuits include features for a powersave mode that require only a quiescent current to retain the data. This can be incorporated along with the other features disclosed above.

While the transmission of the sensor signals in the embodiments is described with respect to wire transmission and wireless transmission, it must be understood that either type of transmission possible in each of the embodiments. A person skilled in the art will recognize that the embodiments of the present invention can employ either type of transmission while retaining their novel character.

Having disclosed a preferred embodiment and the best mode, modifications and variations may be made to the disclosed embodiments while remaining within the scope of the present invention as defined by the following claims.

What is claimed is:

1. An electrocardiogram (ECG) monitor for measuring a patient's ECG comprising:

a plurality of sensors adapted to be placed on the patient's skin to generate a plurality of sensor signals indicative of the patient's heartbeat, said sensors including an amplifier connected to all of said sensors and configured to amplify said sensor signals, combine said sensor signals, and generate an amplified signal, said amplifier being located sufficiently close to at least one of said sensors to promote Faraday shielding;

a processor remote from said sensors and from said amplifier, said processor having a receiver connected to said amplifier to receive said amplified signal and to process said amplified signal to obtain the patient's ECG.

2. The apparatus of claim 1, wherein:

said processor includes means for continuously comparing an ECG against a prior ECG and determining when an abnormal ECG exists, and when said abnormal ECG exists, recording the abnormal ECG and preceding and succeeding normal ECGs.

3. The apparatus of claim 1, wherein:

said processor includes an A/D converter to convert said amplified signal to a digital data signal, a digital delay line to temporarily store a running portion of said digital data signal, and a memory to record portions of said digital data signal.

4. The apparatus of claim 3, wherein:

said processor further includes a comparator to continuously compare an ECG against a prior ECG and determines when an abnormal ECG exists, and when said abnormal ECG exists, to cause said memory to record a portion of the digital data signal representing the abnormal ECG and preceding and succeeding normal ECGs.

5. The apparatus of claim 3, wherein:

said processor further includes a start record button to cause said memory to store selected portions of said digital data signal.

6. The apparatus of claim 3, wherein:

said processor includes a transmitter to transmit the contents of said memory's contents to an output port.

7. The apparatus of claim 1, wherein:

said plurality of sensors include an active sensor, a reference sensor and a neutral sensor; and said amplifier is positioned on said neutral sensor.

8. The apparatus of claim 7, further comprising:

a second active sensor adapted to be placed on the patient's skin to generate a second active sensor signal; and a second amplifier connected to said second active sensor said reference sensor and said neutral sensor, said second amplifier positioned on said neutral sensor and configured to combine and amplify sensor signals from said second active sensor said reference sensor and said neutral sensor and to generate a second amplified signal; and wherein said processor is further configured to receive said second amplified and to process said second amplified signal to obtain the patient's ECG.

9. An electrocardiogram (ECG) monitor for measuring a patient's ECG comprising:

a plurality of sensors adapted to be placed on the patient's skin to generate a sensor signal indicative of the patient's heartbeat, said sensors including an amplifier that is connected to all of said sensors and located sufficiently close to at least one of said sensors to promote Faraday shielding, said amplifier configured to amplify said sensor signals, combine said sensor signals, and generate an amplified signal;

a FM encoder connected to said amplifier to encode said amplified signal and generate an encoded signal; and a transmitter connected to said FM encoder to transmit said encoded signal to a base station to obtain the patient's ECG.

10. The ECG monitor of claim 9, wherein:

said plurality of sensors include an active sensor, a reference sensor and a neutral sensor; and said amplifier is positioned on said neutral sensor.

11. The ECG monitor of claim 10, further comprising:

a second active sensor adapted to be placed on the patient's skin to generate a second active sensor signal; and a second amplifier connected to said second active sensor said reference sensor and said neutral sensor, said second amplifier positioned on said neutral sensor and configured to combine and amplify sensor signals from said second active sensor said reference sensor and said neutral sensor and to generate a second amplified signal; and wherein said FM encoder is configured to encode said second amplified signal and to generate a second encoded signal; and wherein said transmitter is configured to transmit said second encoded signal to said base station to obtain the patient's ECG.

12. An electrocardiogram (ECG) monitor for connecting to a sensor system having a plurality of sensors adapted to be placed on a patient's skin to generate sensor signals indicative of the patient's heartbeat and an amplifier connected to all of the sensors and located sufficiently close to at least one of the sensors to promote Faraday shielding, the amplifier configured to combine and amplify said sensor signals and generate an amplified signal and transmit said amplified signal to an ECG monitor, said ECG monitor comprising:

a processor remote from said amplifier, said processor having a receiver to receive said amplified signal and to process said amplified signal to obtain the patient's ECG.

13. The apparatus of claim 12, wherein:

said processor includes means for tracking said ECG and determining an abnormal ECG and, when said abnormal ECG exists, recording a portion of said abnormal ECG and storing said portion.

14. The apparatus of claim 12, wherein:

said processor includes means for continuously comparing an ECG against a prior ECG and determining when an abnormal ECG exists, and when said abnormal ECG exists, recording the abnormal ECG and preceding and succeeding normal ECGs.

15. The apparatus of claim 14, wherein:

said processor includes an A/D converter to convert said amplified signal to a digital data signal, a digital delay line to temporarily store a running portion of said digital data signal, and a memory to record portions of said digital data signal.

16. The apparatus of claim 14, wherein:

said processor further includes a start record button to cause said memory to store selected portions of said digital data signal stored in said digital delay line.

17. The apparatus of claim 14, wherein:

said processor includes a digital to analog converter to convert said stored digital data to a reconstructed ECG and a transmitter to transmit said reconstructed ECG to an output port.

18. The apparatus of claim 14, wherein:

said processor includes a transmitter to transmit said memory's contents to an output port.

19. The ECG monitor of claim 12, wherein said plurality of sensors include an active sensor, a reference sensor and a neutral sensor, and said amplifier is positioned on said neutral sensor.

20. The ECG monitor of claim 19, wherein said sensor system further has a second active sensor adapted to be placed on the patient's skin to generate a second active sensor signal and a second amplifier connected to said second active sensor, said reference sensor and said neutral sensor, said second amplifier positioned on said neutral sensor and configured to combine and amplify sensor signals from said second active sensor, said reference sensor and said neutral sensor and to generate a second amplified signal and to transmit said second amplified signal to said ECG monitor, wherein:

said processor is configured to receive said second amplified signal to obtain the patient's ECG.

21. A plurality of sensors for sensing a patient's heartbeat, said sensors comprising:

a reference sensor to generate a reference sensor signal indicative of the patient's heartbeat signal;

an active sensor to generate an active sensor signal indicative of the patient's heartbeat signal; and an amplifier connected to said reference sensor and said active sensor, and in close proximity thereto, configured to combine said reference sensor signal and said active sensor signal to generate a combined signal and to amplify said combined signal to generate an amplified signal.

22. The plurality of sensors of claim 21, further comprising:

a second active sensor to generate a second active sensor signal indicative of the patient's heartbeat signal; and a second amplifier connected to said reference sensor and said second active sensor, and in close proximity thereto, configured to combine said reference sensor signal and said second active sensor signal to generate a second combined signal and to amplify said combined signal to generate a second amplified signal.

23. The plurality of sensors of claim 22, further comprising:

a neutral sensor; and wherein said amplifier is further connected to said neutral sensor and positioned on said neutral sensor and configured to combine a neutral sensor signal with said reference sensor signal and said active sensor signal to generate said amplified signal; and wherein said second amplifier is further connected to said neutral sensor and positioned on said neutral sensor and configured to combine said neutral sensor signal with said reference sensor signal and said second active sensor signal to generate said second amplified signal.

24. The plurality of sensors of claim 21, further comprising:

a neutral sensor; and wherein said amplifier is further connected to said neutral sensor and is positioned on said neutral sensor.

25. A method of monitoring a patient's heartbeat using a sensor assembly including a plurality of sensors and an amplifier connected to all the sensors, comprising the steps of:

sensing the patient's heartbeat with said sensors placed on the patient's skin;

generating, with said sensors, sensor signals indicative of the patient's heartbeat;

receiving, from said sensors, said sensor signals in the amplifier;

combining said sensor signals in said amplifier;

generating an amplified signal in said amplifier;

transmitting said amplified signal to a processor having a receiver;

receiving said amplified signal in said receiver; and processing said amplified signal to obtain the patient's ECG.

26. The method of claim 25, wherein:

said processing step includes the steps of continuously comparing an ECG against a prior ECG and determining when an abnormal ECG exists, and when said abnormal ECG exists, recording the abnormal ECG and preceding and succeeding normal ECGs.

27. The method of claim 25, wherein:

said processing step includes the steps of converting said sensor signal to a digital data signal, delaying a portion of said digital data signal in a digital delay line, and storing a portion of said digital data signal in a memory.

28. The method of claim 27, wherein:

said processing step further includes the step of continuously comparing an ECG against a prior ECG and determining when an abnormal ECG exists, and when said abnormal ECG exists, storing a portion of the digital data signal representing the abnormal ECG and preceding and succeeding normal ECGs.

29. The method of claim 27, wherein:

said processing step further includes the step of storing at least a portion of said digital data signal when a start record button is activated.

30. The method of claim 27, wherein:

said processing step includes transmitting said digital data signal stored in said memory to an output port.

31. The method of claim 25, wherein the sensors include an active sensor, a reference sensor and a neutral sensor, and wherein the amplifier is positioned on the neutral sensor.

32. The method of claim 31, wherein said assembly further includes a second active sensor and a second amplifier, and wherein:

said receiving step is performed by the amplifier receiving sensor signals from the active sensor, the reference sensor and the neutral sensor; and said method further comprising the steps of:

receiving, from said second active sensor, said reference sensor and said neutral sensor, second sensor signals in the second amplifier;

combining the second sensor signals in said second amplifier;

generating a second amplified signal in said second amplifier;

transmitting said second amplified signal to said processor having said receiver;

receiving said second amplified signal in said receiver; and processing said second amplified signal to obtain the patient's ECG.

33. A method of monitoring a patient's heartbeat using a sensor assembly including a plurality of sensors and an amplifier, comprising the steps of:

sensing the patient's heartbeat with said sensors placed on the patient's skin;

generating, with said sensors, sensor signals indicative of the patient's heartbeat;

receiving, from said sensors, said sensor signals in said amplifier;

combining said sensor signals in said amplifier;

generating an amplified signal in said amplifier;

FM encoding said amplified signal to generate an encoded signal; and transmitting said encoded signal to a base station to obtain the patient's ECG.

34. The method of claim 33, wherein the sensors include an active sensor, a reference sensor and a neutral sensor, and wherein the amplifier is positioned on the neutral sensor.

35. The method of claim 34, wherein said assembly further includes a second active sensor and a second amplifier, and wherein:

said receiving step is performed by the amplifier receiving sensor signals from the active sensor, the reference sensor and the neutral sensor; and said method further comprising the steps of:

receiving, from said second active sensor, said reference sensor and said neutral sensor, second sensor signals in the second amplifier;

combining the second sensor signals in said second amplifier;

generating a second amplified signal in said second amplifier;

FM encoding said second amplified signal to generate a second encoded signal; and transmitting said second encoded signal to said base station to obtain the patient's ECG.

* * * * *